United States Patent [19]

Armitage et al.

[11] Patent Number: 4,833,143

[45] **Date of Patent: * May 23, 1989**

[54] ANTIDEPRESSANT AMINES

[75] Inventors: Bernard J. Armitage, Nottinghamshire; John R. Housley, Derbyshire; James E. Jeffery; David N. Johnston, both of Nottinghamshire, all of United Kingdom

[73] Assignee: The Boots Company PLC, England

[ * ] Notice: The portion of the term of this patent subsequent to Dec. 16, 2003 has been disclaimed.

[21] Appl. No.: 536,670

[22] Filed: Sep. 28, 1983

[30] Foreign Application Priority Data

Sep. 30, 1982 [GB] United Kingdom ................ 8227901

[51] Int. Cl.[4] ...................... A61K 31/33; A61K 31/44

[52] U.S. Cl. .................................. 514/255; 514/256; 514/357; 514/365; 514/381; 514/383; 514/396; 514/403; 514/432; 514/438; 514/447; 544/330; 544/322; 544/336; 546/304; 546/292; 548/557; 548/558; 548/190; 548/194; 548/337; 548/375

[58] Field of Search ...................... 514/357, 255, 357; 546/333, 334, 304, 292; 544/2

[56] References Cited

U.S. PATENT DOCUMENTS

| | | | |
|---|---|---|---|
| 3,217,012 | 11/1965 | Bachman | 546/334 |
| 3,780,030 | 12/1973 | Morris | 544/2 |
| 3,966,721 | 6/1976 | Huff | 544/2 |
| 4,443,449 | 4/1984 | Jeffrey et al. | 546/346 |

OTHER PUBLICATIONS

Journal of Heterocyclic Chemistry, vol. XII (1975), pp. 49–57.

Ring Handbook-RSF-1984 Edition 60RSF.

Chem. Abstracts, vol. 88, entry 31983u, Carnmalm et al.

*Primary Examiner*—Joseph L. Schofer
*Assistant Examiner*—Peter F. Kulkosky
*Attorney, Agent, or Firm*—Jacobs & Jacobs

[57] ABSTRACT

Compounds of formula I

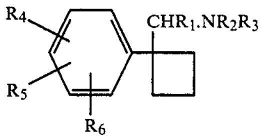

I in which $R_1$ is a heterocyclic ring containing one or more heteroatoms selected from N, O and S;

in which $R_2$ is H, a straight or branched chain alkyl group containing 1 to 4 carbon atoms, an alkenyl group containing 3 to 6 carbon atoms, an alkynyl group containing 3 to 6 carbon atoms or a cycloalkyl group containing 3 to 7 carbon atoms;

in which $R_3$, is H, a straight chain alkyl group containing 1 to 3 carbon atoms or a formyl group in which $R_4$, $R_5$ and $R_6$ which may be the same or different, are H, halo, trifluoromethyl, hydroxy, an alkyl group containing 1 to 3 carbon atoms, an alkoxy group containing 1 to 3 carbon atoms, phenyl or $R_4$ and $R_5$, together with the carbon atoms to which they are attached, form an optionally substituted second benzene ring;

and their pharmaceutically acceptable salts have utility in the treatment of depression. Pharmaceutical compositions and processes for the preparation of compounds of formula I are disclosed.

36 Claims, No Drawings

ANTIDEPRESSANT AMINES

This invention relates to compounds having useful therapeutic activity particularly but not exclusively as antidepressants, to pharmaceutical compositions containing such compounds and to processes for the preparation of such compounds.

The present invention provides compounds of formula I

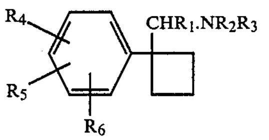

I in which $R_1$ is a heterocyclic ring containing one or more heteroatoms selected from N, O and S;

in which $R_2$ is H, a straight or branched chain alkyl group containing 1 to 4 carbon atoms, an alkenyl group containing 3 to 6 carbon atoms, an alkynyl group containing 3 to 6 carbon atoms or a cycloalkyl group containing 3 to 7 carbon atoms;

in which $R_3$, is H, a straight chain alkyl group containing 1 to 3 carbon atoms or a formyl group in which $R_4$, $R_5$ and $R_6$ which may be the same or different, are H, halo, trifluoromethyl, hydroxy, an alkyl group containing 1 to 3 carbon atoms, an alkoxy group containing 1 to 3 carbon atoms, an alkylthio group containing 1 to 3 carbon atoms, phenyl or $R_4$ and $R_5$, together with the carbon atoms to which they are attached, form an optionally substituted second benzene ring;

and their pharmaceutically acceptable salts.

$R_1$ is a heterocyclic ring which may contain 5 or 6 atoms and may contain one heteroatom (for example furyl, thienyl, pyrrolyl, pyridyl, tetrahydrofuryl or tetrahydrothienyl) or more than one heteroatom which may be the same (for example imidazolyl, pyrazolyl, pyrazinyl, pyrimidinyl, pyridazinyl, triazolyl, tetrazolyl or dithianyl) or different (for example thiazolyl). The heterocyclic ring may be substituted for example by one or more alkyl groups containing 1 to 3 carbon atoms (for example methyl), halo (for example fluoro or chloro), hydroxy, alkoxy groups containing 1 to 3 carbon atoms (for example methoxy) or trifluoromethyl. In preferred compounds of formula I, $R_1$ is a furyl, thienyl, pyridyl, tetrahydrofuryl, dithianyl, methylfuryl, methylpyrrolyl, methylimidazolyl, methylpyrazolyl, methyltetrazolyl or methylthiazolyl group.

When $R_2$ is an alkyl group, the alkyl group may be branched and contains 1 to 4 carbon atoms (for example methyl, ethyl or isopropyl). When $R_2$ is an alkenyl or an alkynyl group, the group contains 3 to 6 carbon atoms (for example allyl or propynyl). When $R_2$ is a cycloalkyl group, the cycloalkyl ring contains 3 to 7 carbon atoms (for example cyclopropyl, cyclobutyl, cyclopentyl or cyclohexyl). When $R_3$ is an alkyl group, the group contains 1 to 3 carbon atoms (for example methyl, ethyl, propyl or isopropyl). In preferred compounds of formula I, $R_2$ is H or methyl and $R_3$ is H, methyl or formyl, When $R_4$, $R_5$ or $R_6$ is a halo group, the halo group may be fluoro, chloro, bromo or iodo. When $R_4$, $R_5$ or $R_6$ is an alkyl, alkoxy or alkylthio group, the group contains 1 to 3 carbon atoms (for example methyl, methoxy or methylthio). When $R_4$ and $R_5$ together with the carbon atoms to which they are attached form a second benzene ring, the second benzene ring may optionally be substituted by halo (for example fluoro, chloro or bromo) or by an alkyl group or an alkoxy group containing 1 to 3 carbon atoms (for example methyl or methoxy) or the substituents on the second benzene ring may together with the carbon atoms to which they are attached form a further benzene ring. In preferred compounds of formula I $R_4$ is a halo group (preferably a chloro, bromo or iodo group) or a methyl group, a methylthio group or a phenyl group and $R_5$ is H, a halo group (preferably a chloro group) or $R_4$ and $R_5$ together with the carbon atoms to which they are attached form a benzene ring.

Compounds of formula I may exist as salts with pharmaceutically acceptable acids. Examples of such salts include hydrochlorides, maleates, acetates, citrates, fumarates, tartrates, succinates and salts with dicarboxylic amino acids such as aspartic and glutamic acids. Salts of compounds of formula I may exist in the form of solvates (for example hydrates).

Compounds of formula I contain one or more chiral centres. Compounds having one chiral centre exist in two enantiomeric forms and the present invention includes both enantiomeric forms and mixtures thereof. Compounds having two or more chiral centres exist in diastereoisomeric forms and the present invention includes each of these diastereoisomeric forms and mixtures thereof.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists'art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known meth ls, for example by the use of cellulose acetate phthala.e. Similarly, capsules, for example hard or soft gelatin capsules, containing the active compound with or without added excipients, may be prepared by conventional means and, if desired, provided with enteric coatings in a known manner. The active material in the capsules may be formulated in a sustained release form. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat depression in human beings. In such treatment the amount of the compound of formula I administered per day is in the range 1 to 1000 mg preferably 5 to 500 mg.

Compounds of formula I may be prepared by the reductive amination of ketones of formula II

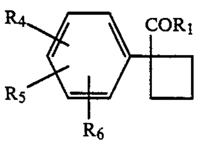

II

Examples of suitable reductive amination processes are given below:

(a) for compounds of formula I in which $R_2$ and $R_3$ are H, by reaction of the ketone with an ammonium salt for example ammonium acetate and a reducing agent such as sodium cyanoborohydride,
(b) for compounds for formula I in which $R_3$ is other than H and $R_2$ is H by reaction of the ketone with an amine of formula $R_3NH_2$ and a reducing agent such as sodium cyanoborohydride or sodium borohydride,
(c) for compounds of formula I in which neither $R_2$ nor $R_3$ is hydrogen by reaction of the ketone with an amine of formula $HNR_2R_3$ and either formic acid or a reducing agent such as sodium cyanoborohydride,
(d) for compounds of formula I in which neither $R_1$ nor $R_2$ contains a reducible double bond by catalytic hydrogenation at elevated temperature and pressure of a mixture of the ketone and an amine of formula $HNR_2R_3$.

Compounds of formula I in which neither $R_2$ nor $R_3$ is H may be prepared by reacting ketones of formula II with formamides of formula $HCONR_2R_3$ for example in the presence of formic acid.

Compounds of formula I may be prepared by the reduction of compounds of formula III

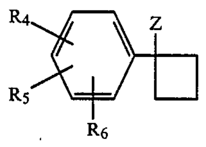

III in which (a) Z is a group of formula $-CR_1{=}NOH$ or an ester or ether thereof to give compounds of formula I in which $R_2$ and $R_3$ are H;
(b) Z is a group of formula $-CR_1{=}NR_2$ (where $R_2$ is not a reducible group) to give compounds of formula I in which $R_3$ is H;
(c) Z is a group of formula $-CR_1{=}NY$ (in which Y represents a metal-containing moiety derived from an organometallic reagent to give compounds of formula I in which $R_2$ and $R_3$ are H.

Suitable reducing agents for the above reactions include sodium borohydride, sodium cyanoborohydride, or lithium aluminium hydride.

In (c) above Y is preferably MgCl or MgBr derived from a Grignard reagent or Li derived from an organolithium compound.

Compounds of formula I in which $R_3$ is H may be prepared by the reaction of an organometallic reagent for example a Grignard reagent of formula $R_1MgX$ where X is Cl, Br or I or an organolithium compound of formula $R_1Li$ with imines of formula IV

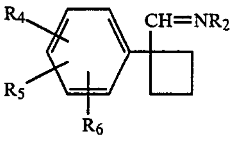

IV followed by hydrolysis to give secondary amines of formula I.

Compounds of formula I in which $R_2$ and $R_3$ are H may be prepared by the decarboxylative rearrangement, for example using iodosobenzene-bistrifluoroacetate or by a Hofmann reaction using bromine in alkaline solution, of amides of formula V

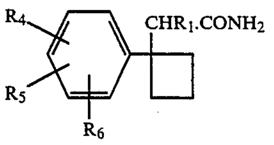

V

Compounds of formula I in which $R_2$ and $R_3$ are H may be prepared by the decarboxylative rearrangement of acyl azides in the Curtius reaction. The acyl azides may be formed for example by reaction of acid chlorides of formula VI with sodium azide.

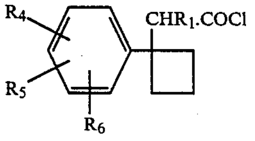

VI

Compounds of formula I in which $R_2$ and $R_3$ are H may be prepared by a Schmidt reaction in which carboxylic acids of formula VII react with hydrazoic acid

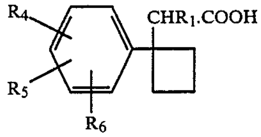

VII

Compounds of formula I in which $R_3$ is H may be prepared by hydrolysis for example acid hydrolysis of compounds of formula I in which $R_3$ is formyl.

Compounds of formula I in which $R_3$ is methyl may be prepared by reduction of compounds of formula I in which $R_3$ is formyl for example by lithium aluminium hydride or by sodium bis(2-methoxyethoxy)aluminum hydride.

Compounds of formula I in which $R_3$ is formyl may be prepared by the reductive amidation of ketones of formula II for example with formamide and formic acid or with ammonium formate and formic acid or with a formamide of formula $HCONHR_2$ and formic acid or with an amine of formula $R_2NH_2$ and formic acid. Compounds of formula I in which $R_3$ is formyl may be prepared by the formylation of compounds of formula I in which $R_3$ is H for example by reaction with methyl formate. Compounds of formula I in which $R_2$ is other than H and $R_3$ is formyl may be prepared by reacting compounds of formula I in which $R_2$ is H and $R_3$ is formyl with a compound of formula $R_2X$ where X is a leaving group such as a halo group in the presence of a base (for example sodium hydride).

Compounds of formula I in which one or both of $R_2$ and $R_3$ is other than H may be prepared from compounds of formula I in which one or both of $R_2$ and $R_3$ are hydrogen by methods which are well known in the art for the conversion of primary to secondary or tertiary amines or for the conversion of secondary to tertiary amines. The following are given as examples of suitable processes:

(a) by alkylating primary amines of formula I to give secondary amines of formula I for example by a process which includes the steps of protecting the primary amine with a protecting group such as trifluoroacetyl, alkylating with an alkyl halide and removing the protecting group for example by hydrolysis;

(b) by alkylating primary amines of formula I, for example, with an alkyl halide to give tertiary amines of formula I in which $R_2$ and $R_3$ are the same;

(c) by alkylating secondary amines of formula I, for example with an alkyl halide to give tertiary amines of formula I in which $R_2$ and $R_3$ may be different;

(d) by reacting primary amines of formula I with sodium borohydride and a carboxylic acid of formula $CH_3(CH_2)_aCOOH$ in which a is 0, 1 or 2 to give secondary amines of formula I in which $R_2$ is a group of formula $CH_3(CH_2)_{a+1}$ and $R_3$ is H or tertiary amines of formula I in which both $R_2$ and $R_3$ are a group of formula $CH_3(CH_2)_{a+1}$;

(e) by reacting primary amines of formula I with formaldehyde and formic acid to give tertiary amines of formula I in which both $R_2$ and $R_3$ are methyl;

(f) by reacting secondary amines of formula I in which $R_3$ is H with formaldehyde and formic acid to give tertiary amines of formula I in which $R_3$ is methyl;

(g) by formylating primary amines of formula I, for example by reaction with methyl formate to give compounds of formula I in which $R_3$ is formyl and reducing the formamides, for example with lithium aluminium hydride to give secondary amines of formula I in which $R_2$ is H and $R_3$ is methyl;

(h) by formylating secondary amines of formula I, for example by reaction with methyl formate, to give compounds of formula I in which $R_3$ is formyl and reducing the formamides, for example with lithium aluminium hydride to give tertiary amines of formula I in which $R_3$ is methyl;

(i) by acylating primary amines of formula I, for example by reaction with an acyl chloride of formula $R_7COCl$ or an anhydride of formula $(R_7CO)_2O$ in which $R_7$ is an alkyl, alkenyl or alkynyl group and reducing the resulting amides for example with lithium aluminium hydride to give secondary amines of formula I in which $R_2$ is $—CH_2R_7$ and $R_3$ is H;

(j) by acylating secondary amines of formula I in which $R_2$ is H for example by reaction with an acyl chloride of formula $R_7COCl$ or an anhydride of formula $(R_7CO)_2O$ and reducing the resulting amides for example with lithium aluminium hydride to give tertiary amines in which $R_2$ is $—CH_2R_7$;

(k) by reacting primary amines of formula I with aldehydes of formula $R_8CHO$ in which $R_8$ is an alkyl, alkenyl or alkynyl group and reducing the resulting imines for example with sodium cyanoborohydride or, if $R_8$ and $R_1$ do not contain reducible double bonds, by catalytic hydrogenation to give secondary amines of formula I in which $R_2$ is $—CH_2R_8$ and $R_3$ is H;

(l) by reacting primary amines of formula I with ketones of formula $R_9COR_{10}$ in which $R_9$ and $R_{10}$, which may be the same or different are alkyl groups or $R_9$ and $R_{10}$ together with the carbon atom to which they are attached form an alicyclic ring and reducing the resulting imines for example with sodium cyanoborohydride or, if $R_1$, $R_9$ and $R_{10}$ do not contain reducible double bonds, by catalytic hydrogenation to give compounds of formula I in which $R_3$ is H and $R_2$ is a group of formula VIII

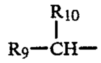

VIII (m) by reacting secondary amines of formula I in which $R_2$ is H with aldehydes of formula $R_8CHO$ in which the group $R_8$ has a hydrogen atom on the carbon atom adjacent the formyl group, and reducing the resulting enamines for example with sodium cyanoborohydride or, when $R_8$ and $R_1$ do not contain reducible double bonds, by catalytic hydrogenation to give secondary amines of formula I in which $R_2$ is $—CH_2R_8$;

(n) by reacting secondary amines of formula I in which $R_3$ is H with ketones of formula $R_9COR_{10}$ in which one of the groups $R_9$ and $R_{10}$ has a hydrogen atom on the carbon atom adjacent the carbonyl group and reducing the resulting enamines for example with sodium cyanoborohydride or when $R_1$, $R_9$ and $R_{10}$ do not contain reducible double bonds, by catalytic hydrogenation to give compounds of formula I in which $R_2$ is a group of formula VIII;

Compounds of formula I in which the group $R_1$ contains one or more double bonds may be reduced, for example by catalytic hydrogenation, to give compounds of formula I in which $R_1$ is a saturated heterocyclic group.

The group $R_1$ may be built up by methods well known in the art. For example, when $R_1$ is a heterocyclic ring containing four nitrogen atoms and is substituted by an alkyl group, compounds of formula I may be prepared from cyano compounds of formula IX

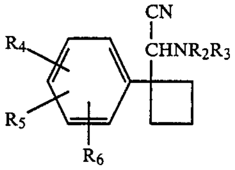
IX for example by reaction of cyano compounds of formula IX with sodium azide and aluminium chloride to give compounds of formula I in which $R_1$ is a tetrazole group followed by alkylation.

The ketones of formula II may be prepared by the hydrolysis of compounds of formula III in which Z is $-CR_1=NH$ or by the acid hydrolysis of imines of formula X

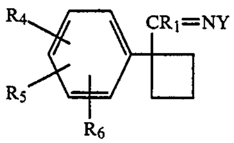
X in which Y represents a metal-containing moiety derived from an organometallic reagent. The imines of formula X may be prepared by the reaction of said organometallic reagent with cyano compounds of formula XI

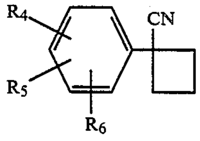
XI

Suitable organometallic reagents include Grignard reagents of formula $R_1MgX$ where X is Cl, Br or I (Y=MgX) and organolithium compounds of formula $R_1Li$ (Y=Li).

Ketones of formula II may be prepared by the reaction of carboxylic acid derivatives such as amides or acid halides with an organometallic reagent for example by the reaction of an acid chloride of formula XII

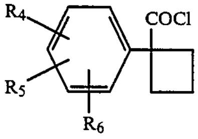
XII with a Grignard reagent of formula $R_1MgX$ where X is Cl, Br or I at low temperatures or by the reaction of carboxylic acids of formula XIII

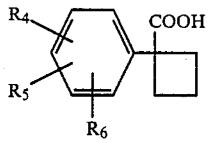
XIII with an organometallic reagent, for example an organolithium compound of formula $R_1Li$.

Compounds of formula III in which Z is a group of formula $-CR_1=NOR$ or ethers or esters thereof may be prepared by the reaction of hydroxylamine or an ether or ester thereof with ketones of formula II.

Compounds of formula III in which Z is a group of formula $-CR_1=NR_2$ may be prepared by the reaction of amines of formula $R_2NH_2$ with ketones of formula II or, when $R_2=H$, by the hydrolysis of compounds of formula III in which Z is a group of formula $-CR_1=NY$.

The preparation of compounds of formula III in which Z is a group of formula $-CR_1=NY$ has been described above in respect of compounds of formula X.

Imines of formula IV may be prepared by reaction of amines of formula $R_2NH_2$ with aldehydes of formula XIV

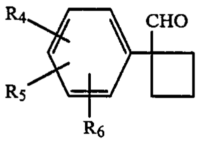
XIV

Amides of formula V may be prepared by the reaction of ammonia with carboxylic acid derivatives for example acid chlorides of formula VI or they may be prepared from cyano compounds of formula XV for example by hydration with aqueous acids or by reaction with hydrogen peroxide in the presence of a base.

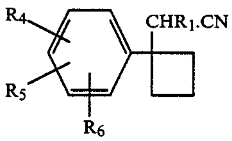
XV

Carboxylic acids of formula VII and XIII may be prepared by the hydrolysis, for example basic hydrolysis, of cyano compounds of formula XV and XI respectively. Carboxylic acids of formula VII may be prepared by the reaction of amides of formula V with nitrous acid. Carboxylic acids of formula XIII may be prepared by the reaction of nitrous acid with the amides formed by (a) the reaction of ammonia with carboxylic acid derivatives for example acid chlorides of formula XII or (b) by the reaction of cyano compounds of formula XI with hydrogen peroxide in the presence of a base.

Cyano compounds of formula IX may be prepared by one of the following reactions:

(a) by the reaction of cyano compounds of formula XI with an aluminium hydride, for example diisobutylaluminium hydride, to form compounds of formula III in which Z is a group of formula $-CH=NAl^{i}Bu_2$ followed by reaction of these compounds with cyanide ion and hydroylsis to give the cyano compounds of formula IX in which both $R_2$ and $R_3$ are H, or (b) by the reaction of aldehydes of formula XIV with an alkali metal cyanide and an amine of formula $NHR_2R_3$.

Cyano compounds of formula XI may be prepared by the reaction of cyano compounds of formula XVI

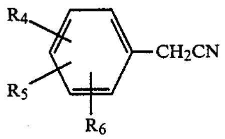

XVI with a 1,3-disubstituted propane for example 1,3-dibromopropane and a base such as sodium hydride.

Cyano compounds of formula XV may be prepared from the cyano compounds of formula XVII

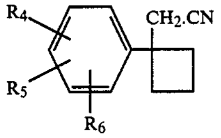

XVII for example by reaction with a halide of formula $R_1X$ where X is chloro, bromo or iodo in the presence of a base such as lithium diisopropylamide.

Cyano compounds of formula XV may also be prepared by reacting ketones of formula II with a reagent for introducing a cyano group such as p-toluene-sulphonylmethyl isocyanide.

Cyano compounds of formula XVII may be prepared from cyano compounds of formula XI by for example the following series of reactions:

(a) hydrolysis of the cyano group to form a carboxylic acid of formula XIII or alcoholysis of the cyano group to form an ester of a carboxylic acid of formula XIII;

(b) reduction of the carboxylic acid or the ester thereof for example with lithium aluminium hydride or borane-dimethylsulphide complex to form the corresponding alcohol;

(c) replacement of the hydroxy group of the alcohol by a leaving group for example a p-toluenesulphonyloxy group and (d) replacement of the leaving group with a cyano group.

Acid chlorides of formula XII and VI may be prepared by the reaction of carboxylic acids of formula XIII and VII respectively with for example thionyl chloride.

Aldehydes of formula XIV may be prepared by methods well known to those skilled in the art. The following are given as examples of suitable methods:

(a) by the reduction of cyano compounds of formula XI with for example, di-tert-butylaluminium hydride or diisobutylaluminium hydride followed by hydrolysis.

(b) by the reduction of carboxylic acid derivatives, for example (i) by the reduction of tertiary amides formed by the reaction of secondary amines with acid chlorides of formula XII, for example when the secondary amine is a dialkylamine using lithium diethoxyaluminohydride as a reducing agent or when the secondary amine is ethyleneimine using lithium aluminium hydride as the reducing agent, (ii) by the reduction of acid chlorides of formula XII for example, with lithium tri-tert-butoxyaluminohydride.

(c) by the oxidation of alcohols (prepared by the reduction of carboxylic acids of formula XIII) with, for example, chromium trioxide-pyridine complex in dichloromethane under anhydrous conditions.

Ketones of formula II, the compounds of formula III, the amines of formula X, the amides of formula V, the acid chlorides of formula VI, the carboxylic acids of formula VII and the cyano compounds of formula XV are described herein as intermediates are novel compounds.

The therapeutic activity of the compounds of formula I has been indicated by assessing the ability of the compounds to reverse the hypothermic effects of reserpine in the following manner. Male mice of the Charles River CDl strain weighing between 18 and 30 grammes were separated into groups of five and were supplied with food and water ad libitum. After five hours the body temperature of each mouse was taken orally and the mice were injected intraperitoneally with reserpine (5 mg/kg) in solution in deionised water containing ascorbic acid (50 mg/ml). The amount of liquid injected was 10 ml/kg of body weight. Nine hours after the start of the test food was withdrawn by water was still available ad libitum. Twenty-four hours after the start of the test the temperatures of the mice were taken and the mice were given the test compound suspended in a 0.25% solution of hydroxy ethyl cellulose (sold under the trade name Cellosize QP 15000 by Union Carbide) in deionised water at a dose volume of 10 ml/kg of body weight. Three hours later the temperatures of all the mice were again taken. The percentage reversal of the reserpine-induced loss of body temperature is then calculated by the formula:

$$\frac{(T_{27} - T_{24})}{(T_5 - T_{24})} \times 100$$

in which $T_t$ is the temperature in degrees Celsius after t hours. The mean value for each group of five mice was taken at several dose rates to enable a value of the mean dose which causes a 50% reversal (ED50) to be obtained. All the compounds which are the final products of the Examples hereinafter gave values of ED50 of 30 mg/kg or less. It is widely understood by those skilled in the art that this test is indicative of compounds having antidepressant activity in humans.

The invention will now be illustrated by the following Examples which are given by way of example only. All compounds were characterised by conventional analytical techniques and gave satisfactory elemental analyses. All melting and boiling points are expressed in degrees Celsius.

EXAMPLE 1

Thiophene (10 ml) was added to a solution of butyllithium in dry ether (60 ml) (prepared by the reaction of lithium (1.8 g) and butyl-bromide (14 g) followed by filtration through glass wool) and the mixture heated under reflux for 2 hours. A solution of 1-(4-chlorophenyl)cyclobutanecarbonitrile (15 g) in dry ether (20 ml) was added dropwise and the mixture heated under reflux for 75 minutes. After cooling to −10° C. a mixture of ice and water (30 ml) and then ice-cold 5N hydrochloric acid (50 ml) were added. Toluene (100 ml) was added and the mixture heated under reflux for 3 hours. The toluene layer was separated, dried and the solvent removed by evaporation to give a residue which was distilled at 156° C. at 0.05 mm Hg to give [1-(4-chlorophenyl)cyclobutyl](thien-2-yl) ketone (m.p. 74°-76° C.).

A mixture of the ketone (2.77 g) prepared as above, formamide (10 ml) and 98% formic acid (2 ml) was heated at 190° C. for 17 hours. The mixture was cooled and extracted with dichloromethane. The extract was washed, dried and the solvent removed to yield an oil which solidified to give N-formyl-[1-(4-chlorophenyl)-cyclobutyl](thien-2-yl)methylamine (m.p. 114°-119° C.).

The N-formyl compound (1.55 g) prepared as above was added to a mixture of concentrated hydrochloric acid (10 ml), water (10 ml) and diethyleneglycoldimethyl ether (20 ml) and the reaction mixture heated to 140° C. for 4 hours 30 minutes. The reaction mixture was poured into water (300 ml), aqueous sodium hydroxide was added and the resulting basic mixture extracted with ether. The ether extract was washed with water and extracted with 1M hydrochloric acid. The acid extract was washed with ether, basified with aqueous sodium hydroxide and extracted with ether. Hydrogen chloride gas was passed through the dried ether extract to give [1-(4-chlorophenyl)cyclobutyl](thien-2-yl)methylamine hydrochloride (m.p. 238°-240° C.).

EXAMPLE 2

A solution of 2-bromopyridine (12.3 g) in dry ether (80 ml) was added to a 1.55M solution of butyllithium in hexane (30 ml) at −78° C. The mixture was stirred at −78° C. for one hour and a solution of 1-(4-chlorophenyl)cyclobutanecarbonitrile (8 g) in ether (8 ml) added and the temperature of the mixture was allowed to rise to ambient. After one hour a solution of sodium borohydride (3 g) in dry diethyleneglycoldimethyl ether (130 ml) was added and the mixture heated at 95° C. for two hours. Water (100 ml) was added and the mixture extracted with ether. The ether extract was extracted with 8N hydrochloric acid and the acid extract washed with ether, basified with aqueous sodium hydroxide solution and extracted with ether. The ether extract was filtered through diatomaceous earth, dried and the solvent removed by evaporation. The residue was distilled in the range 168°-180° C. at 0.2 mm Hg pressure to yield an oil which was dissolved in ether. Hydrogen chloride gas was passed through the ethereal solution and the resulting precipitate was heated with propan-2-ol to give [1-(4-chlorophenyl)cyclobutyl](pyrid-2-yl)methylamine dihydrochloride (m.p. 240°-245° C. (dec)).

In a similar manner to that described above the following compounds were prepared 2(a) [1-(4-Chlorophenyl)cyclobutyl](pyrid-3-yl)methylamine dihydrochloride (m.p. 275°-280° C.)

2(b) [1-(4-Chlorophenyl)cyclobutyl](pyrid-4-yl)methylamine dihydrochloride (m.p. 260°-265° C.)

EXAMPLE 3

A solution of 2-bromopyridine (4.8 g) in dry ether (30 ml) was added to a 1.7M solution of butyllithium in hexane (18 ml) at −78° C. with stirring. After one hour at that temperature a solution of 1-(4-biphenylyl)cyclobutanecarbonitrile (4 g) in a mixture of dry ether (80 ml) and dry tetrahydrofuran (10 ml) was added and the temperature allowed to rise to 0° C. After cooling to −20° C., methanol (20 ml) and then water (30 ml) were added dropwise. The aqueous mixture was extracted with ether and the ether extract washed, dried and evaporated to give [1-(4-biphenylyl)cyclobutyl](pyrid-2-yl)methanimine as an orange oil. The oil was dissolved in propan-2-ol (200 ml) and heated under reflux with sodium borohydride (2.0 g) for five hours. Water was added and the propan-2-ol removed by evaporation. The aqueous residue was extracted with ether. Hydrogen chloride gas was passed into the dried ether extract to give a gum which was heated with propan-2-ol to give a white solid which was recrystallised from a mixture of methanol and propan-2-ol to give [1-(4-biphenylyl)cyclobutyl](pyrid-2-yl)methylamine dihydrochloride hydrate (m.p. 240° C. (dec)).

In a similar manner to that described above compounds of formula XVIII listed in Table 1 were prepared.

TABLE 1

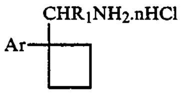

XVIII

| Example | Ar | $R_1$ | n | Melting point °C. | Notes |
|---|---|---|---|---|---|
| 3a | 3-trifluoromethylphenyl | 3-pyridyl | 2 | 265° (dec) | |
| 3b | 4-chlorophenyl | 3-thienyl | 1 | 253-255° | (1) (2) |
| 3c | 4-chloro-3,5-dimethylphenyl | 2-pyridyl | 2 | 238-242° | (3) |
| 3d | 3,4-dichlorophenyl | 2-pyridyl | 2 | 271-273° (dec) | (3) |
| 3e | 4-methylthiophenyl | 3-pyridyl | 1.1 | 253-257° | (3) (4) (5) (6) (8) |
| 3f | 4-fluorophenyl | 2-thienyl | 1 | 230-233° | (4) (5) (8) (9) |
| 3g | 6-chloro-2-naphthyl | 2-pyridyl | 2 | 208-212° | (3) (4) (5) (7) (8) |

TABLE 1-continued

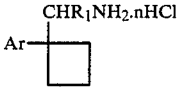

XVIII

| Example | Ar | $R_1$ | n | Melting point °C. | Notes |
|---|---|---|---|---|---|
| 3h | 4-chloro-2-fluorophenyl | 3-pyridyl | 2 | 276–279° | (3) (4) (5) (8) |

Notes to Table 1
(1) imine purified by distillation and isolated as its hydrochloride salt
(2) the sodium borohydride was added in diethyleneglycoldimethyl ether
(3) the sodium borohydride was added in ethanol
(4) carbonitrile added in ether solution
(5) after reduction the solvent was removed by distillation and the residue dissolved in ether. The ether solution was then washed with water
(6) salt contains 0.67 moles of water
(7) hemihydrate - recrystallised from propan-2-ol
(8) butyllithium added at −70° C.; methanol added at −40° C.
(9) product recrystallised from a mixture of ethanol and petroleum ether (b.p. 60–80° C.).

EXAMPLE 4

1-Methylpyrazole (4.8 g) was added to a mixture of dry ether (60 ml) and a 1.7M solution of butyllithium in hexane (30 ml) under nitrogen at a temperature of less than 5° C. N,N,N'N'-Tetramethylethylenediamine (TMEDA) (8.3 g) was added and the mixture stirred at 0°–5° C. for one and three quarter hours and then 1-(4-chlorophenyl)cyclobutanecarbonitrile (6.0 g) was added and the mixture stirred for 90 minutes at a temperature in the range 0 to 5° C. Water was added and the reaction mixture extracted with ether. The extract was washed, dried and evaporated to give an oil which is [1-(4-chlorophenyl)cyclobutyl](1-methylpyrazol-5yl)methanimine. The imine was stirred with a mixture of sodium borohydride (2 g) in diethyleneglycol-dimethyl ether (100 ml) under nitrogen at 95° C. for two hours. The mixture was poured into water and extracted with ether. The extract was washed, dried and evaporated to give a residue which was dissolved in dry ether. Hydrogen chloride gas was passed through the ethereal solution to give a hydrochloride salt of [1-(4-chlorophenyl)cyclobutyl](1-methylpyrazol-5-yl)methylamine hydrochloride (m.p. 316°–318° C.) containing 1.25 moles of hydrochloride and 0.25 moles of water.

The compounds of formula XVIII listed in Table 2 were prepared in a similar manner to that described above except that the reaction between the heterocycle and the butyllithium took place at 40° C. Other modifications of the above method are indicated by notes to Table 2.

TABLE 2

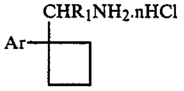

XVIII

| Example No. | Ar | $R_1$ | n | Notes | m.p. of HCL salt of amine |
|---|---|---|---|---|---|
| 4a | 4-chlorophenyl | 5-methylfur-2-yl | 1 | (1) (5) | 218–219° C. (dec) |
| 4b | 4-chlorophenyl | 2-furyl | 1 | (2) (5) | 230° C. (dec) |
| 4c | phenyl | 2-thienyl | 1 | (2) (5) | 225–230° C. (dec) |
| 4d | 4-biphenylyl | 2-thienyl | 1 | (1) (5) (6) | 165–170° C. |
| 4e | 4-chlorophenyl | 1-methylpyrrol-2-yl | 1 | (3) (4) | |
| 4f | 3,4-dichlorophenyl | 1-methylimidazol-2-yl | 2 | (5) (7) (8) | 259–261° C. |

Notes
(1) imine isolated as its hydrochloride salt
(2) a solid containing the imine or a salt of the imine was precipitated by the addition of a solution acetic acid in ether
(3) the product was separated as the free base by high pressure liquid chromatography. The physical constants of the product were not determined
(4) the imine intermediate has an ED50 of less than 30 mg/kg when determined in the test described hereinbefore
(5) No TMEDA used
(6) the sodium borohydride was added in propan-2-ol.
(7) the sodium borohydride was added in ethanol.
(8) the reaction between the heterocycle and the butyllithium took place at 0° C.

EXAMPLE 5

A solution of 2-bromothiophene (32.9 g) in dry ether (50 ml) was added dropwise to a stirred mixture of magnesium turnings (4.85 g) and ether (50 ml) under nitrogen. When all the magnesium had dissolved a solution of 1-(3,4-dichlorophenyl)cyclobutanecarbonitrile (30.6 g) in dry ether (200 ml) was added and the mixture stirred at 20° C. for one hour and then heated under reflux for one hour. A solid formed which is believed to be 1-(3,4-dichlorophenyl)cyclobutyl](thien-2-yl)methaniminylmagnesium bromide and was collected by filtration. The solid was dissolved in ethanol (200 ml) and a solution of sodium borohydride (10 g) in ethanol (500 ml) added and the mixture heated under reflux for four hours. The mixture was cooled and water (200 ml) and then 5N hydrochloric acid added. The ethanol was removed by evaporation and the aqueous solution basified by the addition of 5N sodium hydroxide solution. The aqueous layer was extracted with ether and the extract dried. Hydrogen chloride gas was passed into the ethereal solution to give [1-(3,4-dichlorophenyl)cyclobutyl](thien-2-yl)methylamine hydrochloride (m.p. 238°–242° C.).

The compounds of formula XVIII listed in Table 3 were prepared in a similar manner to that described above.

TABLE 3

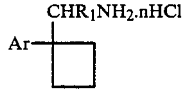

XVIII

| Example No. | Ar | $R_1$ | Notes | n | m.p. |
|---|---|---|---|---|---|
| 5a | 4-chlorophenyl | 2-thienyl | | 1 | 238-240° C. |
| 5b | 4-chlorophenyl | 1-methylimidazol-2-yl | (1) (2) (4) | 0 | 93-94° C. |
| 5c | 2-naphthyl | 1-methylimidazol-2-yl | (1) (3) (4) | 0 | 126-129° C. |
| 5d | 4-methylphenyl | 2-thienyl | (5) | 1 | 228-230° C. |
| 5e | 4-methoxyphenyl | 2-thienyl | | 1 | 192-195° C. |
| 5f | 4-bromophenyl | 2-thienyl | | 1 | 235-237° C. |
| 5g | 4-iodophenyl | 2-thienyl | | 1 | 228-230° C. |

Notes
(1) 1-methylimidazolylmagnesium bromide was prepared et al J. Het. Chem. 12 49-57 (1975) et al. J. Het. Chem. 1953 20 p. 702-707
(2) the free base was obtained by distillation (boiling point range 160 to 170° at 0.1 mm Hg) and recrystallised from cyclohexane
(3) the sodium borohydride was in solution in diethyleneglycoldimethyl ether
(4) Grignard reagent made in tetrahydrofuran solvent
(5) iminylmagnesium bromide not isolated as a solid. The ether was removed by evaporation and the residue heated under a nitrogen atmosphere at 90-95° C. for an hour. The treated residue was dissolved in ethanol.

EXAMPLE 6

A solution of 4-methylthiazole (4.95 g) in ether (5 ml) was added to ethylmagnesium bromide prepared under nitrogen from magnesium turnings (1.2 g) and ethyl bromide (5.5 g) in ether (40 ml). A yellow precipitate was formed which dissolved when the ether was replaced by tetrahydrofuran (70 ml). 1-(4-Chlorophenyl)-cyclobutanecarbonitrile (6.0 g) was added and the solvent replaced by toluene and the mixture heated at 90° C. for two hours. Water and 2N sodium hydroxide solution were added and the reaction mixture extracted with ether. The extract was dried and the solvents removed by evaporation. The residue was dissolved in ether and hydrogen chloride gas was passed into the solution to give a pale yellow solid which is believed to be [1-(4-chlorophenyl)cyclobutyl](4-methylthiazol2-yl)methanimine hydrochloride. This salt was heated at 95° C. for two hours with a solution of sodium borohydride (2 g) in diethyleneglycoldimethylether (100 ml). Water and 2N sodium hydroxide solution were added and the reaction mixture extracted with ether. The extract was dried and the solvents removed by evaporation. The residue was dissolved in ether and hydrogen chloride gas was passed into the solution to give a yellow solid. This solid was converted into the free base which was purified by column chromatography on a florisil column eluted with a mixture of ether and cyclohexane to give [1-(4-chlorophenyl)cyclobutyl](4-methylthiazol-2-yl)methylamine which was converted into a hydrochloride salt [m.p. 230°-232° C. (dec)]containing 1.5 moles of hydrochloride by dissolving the free base in ether and passing hydrogen chloride gas through the solution.

EXAMPLE 7

The product of Example 5(a) in the form of its free base (2.0 g), 98% formic acid (8 ml) and 37-40% aqueous formaldehyde solution (16 ml) was stirred at 20° C. for one hour and then heated to 55°-60° C. for one hour and volatile materials were evaporated at 95° C. and atmospheric pressure. The residue was basified with aqueous sodium hydroxide solution and extracted with ether. Hydrogen chloride gas was bubbled through the dried ethereal solution to deposit an oil. The solvent was evporated and the residue triturated with dry ether and clarified by filtration. The filtrate was evaporated and the residue triturated with dry acetone to give N,N-dimethyl-[1-(4-chlorophenyl)cyclobutyl](thien-2-yl)methylamine hydrochloride (m.p. 185°-190° C.).

EXAMPLE 8

Acetic anhydride (5 ml) was added to a mixture of the product of Example 5(a) in the form of its free base (3 g) and crushed ice (5 g) and the resulting mixture stirred for 5 minutes. Aqueous sodium hydroxide (5N) was added and the resulting basic mixture extracted with ether. The ether extract was washed with water, dried and the ether removed by evaporation to give a residue which was triturated with petroleum ether (b.p. 60°-80° C.) to give a solid which was crystallised from petroleum ether (b.p. 80°-100° C.) to give N-acetyl-[1-(4-chlorophenyl)cyclobutyl](thien-2-yl)methylamine (m.p. 105°-108° C.).

Borane-dimethylsulphide complex (2 ml) was added dropwise to a solution of the N-acetyl compound (prepared as above) (1.5 g) in dry tetrahydrofuran. The mixture was stirred for 30 minutes at 20° C. and at 40°-45° C. for 10 minutes. Water was added to the cooled reaction mixture which was then extracted with ether. Hydrogen chloride gas passed into the dried ether extract to give a solid which was heated with boiling ether. The material which did not dissolve was N-ethyl-[1-(4-chlorophenyl)cyclobutyl]-(thien-2-yl)methylamine hydrochloride (m.p. 204°-207° C.).

EXAMPLE 9

A 1.7M solution of butyllithium in hexane (30 ml) was added under nitrogen to a stirred solution of diisopropylamine (5.2 g) in dry ether (20 ml) at 20° C. After 20 minutes the mixture was cooled to −20° C. and a solution of 1,3-dithiane (6 g) in dry ether (50 ml) added dropwise. A solution of 1-(4-chlorophenyl)cyclobutane carbonitrile (6 g) in dry ether (20 ml) was added. The temperature was maintained at 0° C. for 20 minutes. Sodium borohydride (2 g) in dry diethyleneglycol dimethyl ether (150 ml) was added and the mixture heated at 95° C. for two hours. Water was added and an ether extraction performed. The extract was washed, dried and evaporated to yield a residue which was dissolved in ether. [1-(4-Chlorophenyl)cyclobutyl](1,3-dithian-2-yl)methylamine hydrochloride (m.p. 165°-167° C. (dec)) was precipitated by passing hydrogen chloride gas into the ether extract.

EXAMPLE 10

The product of Example (4)b (1.49 g) was dissolved in absolute ethanol (45 ml) and Raney nickel (approximately 3 ml) added. The mixture was stirred under an atmosphere of hydrogen for two hours and thirty minutes and the reaction mixture was filtered and the solvent removed by evaporation. The residue was dissolved in dilute hydrochloric acid and the solution basified. A white solid formed which was extracted into ether. The extract was dried and yielded [1-(4-chlorophenyl)cyclobutyl](tetrahydrofur2-yl)methylamine as an oil (Physical constants not determined).

EXAMPLE 11

The product of Example 3 in the form of its free base was mixed with methyl formate and the mixture stored at ambient temperature for 4 days. A gum formed which was triturated with petroleum ether with warming to give N-formyl-[1-(4-biphenylyl)cyclobutyl](pyrid-2-yl)methylamine (m.p. 101° C.).

EXAMPLE 12

A 1M solution of diisobutylaluminium hydride in hexane (200 ml) was added at −30° C. to a solution of 1-(4-chlorophenyl)cyclobutanecarbonitrile (38.3 g) in ether (200 ml) under nitrogen. The temperature was maintained at −5° C. for two hours and then cooled to −20° C. Finely powdered sodium cyanide (12.25 g), finely powdered ammonium chloride (51.1 g) and dimethylsulphoxide (200 ml) were added sequentially and the mixture warmed to ambient temperature. 18-Crown-6 (1 g) was added and the mixture stirred for 16 hours. After 5 hours rapid stirring, water (8 ml) was added dropwise and the stirring continued for 16 hours. Water (100 ml) was then added in ten portions and the reaction mixture poured into 2N aqueous sodium hydroxide solution (500 ml). An ether extraction was performed and the extract dried. Hydrogen chloride gas was passed through the extract to give a pale yellow solid which was recrystallised from propan-2-ol to give 1-amino-1-[1-(4-chlorophenyl)-cyclobutyl]acetonitrile hydrochloride hydrate.

Finely powdered sodium azide (19 g) was added to a solution of aluminium chloride (13.35 g) in tetrahydrofuran (120 ml) under nitrogen and the mixture heated under reflux for 30 minutes. The acetonitrile salt (13.75 g) prepared as described above was added and the mixture heated under reflux with stirring for 70 hours. After cooling the reaction mixture, water (200 ml), concentrated hydrochloric acid (200 ml) and water (500 ml) were added sequentially and the mixture heated to 90°-95° under vacuum to reduce the volume. An oil and sodium chloride separated from the reaction mixture. These were discarded and the filtrate was evaporated to give a white solid which was stirred with isopropanol (200 ml) and the mixture filtered. The solvent was removed from the filtrate and the residue dissolved in water (150 ml). A solid was precipitated by the addition of aqueous ammonia solution and a sample of this solid (5 g) in finely ground form was added to a mixture of acetone (30 ml) and water (200 ml). The mixture was made strongly alkaline by adding potassium hydroxide solution and then dimethyl sulphate (20 ml) was added dropwise over three hours. The pH was maintained at 10. The mixture was stirred at ambient temperature for sixteen hours and excess concentrated aqueous ammonia solution added. The mixture was extracted with ether. The ether extract was dried and the ether removed. Hydrogen chloride gas was passed through an ethereal solution of the residue to give a solid which was dissolved in methanol. The methanol was removed by evaporation. The residue was dissolved in propan-2-ol and the solvent removed by evaporation to give a hydrochloride salt containing 90% N-methyl-[1-(4-chlorophenyl)cyclobutyl](1-methyl-5tetrazolyl)methylamine and 10% N-methyl-[1-(4-chlorophenyl)cyclobutyl](2-methyl-5-tetrazolyl)methylamine. The salt contained 1.1 moles HCl (m.p. 230° C.(dec)).

EXAMPLE 13

The product of Example 3(d) in the form of its free base (3 g) and cyclopentanone (1.65 g) were mixed at room temperature, then heated with stirring at 140° C. for 18 hours. The mixture was then cooled to room temperature dissolved in the minimum amount of ethanol ( 200 ml), and treated with a suspension of sodium borohydride (2 g) in ethanol (20 ml). The mixture was heated under reflux for 2 hours left at room temperature for 16 hours and the solvent removed. The residue was diluted with water, acidified with 2N hydrochloric acid, basified with 2N aqueous sodium hydroxide, and extracted with ether. The extracts were washed and dried and the solvent removed to leave an oil which was purified by chromatography to give a pale brown gum which was taken up in ether and saturated with hydrogen chloride to give N-{[1-(3,4-dichlorophenyl)-cyclobutyl](2-pyridyl)methyl}cyclopentylamine sesquihydrochloride (m.p. 120°-122° C.).

EXAMPLE 14

A mixture of the compound of Example 4f in the form of its free base (3 g), acetone (1 g), sodium cyanoborohydride (1.1 g) and methanol was stirred at ambient temperature for seven days. The solvent was removed by evaporation and water added. The aqueous mixture was extracted with ether. Evaporation of the washed and dried extract gave a white solid which was purified by chromatography on a silica column eluted with a mixture of ether (9 parts) and methanol (1 part) as eluant to give N-{[1-(3,4-dichlorophenyl)cyclobutyl](1-methylimidazol-2-yl)methyl}-1-methylethylamine (m.p. 98°-100° C.).

EXAMPLE 15

In a similar manner to that described in Example 14, N-{[1-(3,4-dichlorophenyl)cyclobutyl](pyrid-2-yl)methyl}-1-methylethylamine was obtained as an oil, the physical characteristics of which were not determined.

EXAMPLE 16

Pharmaceutical compositions containing any one of the compounds of formula I disclosed in Examples 1 to 15 are prepared in the following manner.

EXAMPLE 16(a)

Tablets are prepared from the following ingredients:

| | Parts by Weight |
|---|---|
| Active Ingredient | 50.0 |
| Lactose | 78.5 |
| Polyvinylpyrrolidone | 5.0 |
| Maize Starch | 15.0 |
| Magnesium Stearate | 1.5 |

The active ingredient, the lactose and some of the starch are mixed and granulated with a solution of the polyvinylpyrrolidone in etahnol. The granulate is mixed with the stearic acid and the rest of the starch and the mixture is compressed in a tabletting machine to give tablets containing 50.0 mg of the active ingredient.

EXAMPLE 16(b)

Capsules are prepared in the following way. A mixture of the active ingredient (45 parts by weight) and lactose powder (205 parts by weight) is filled into hard gelatin capsules, each capsule containing 45 mg of the active ingredient.

EXAMPLE 16(c)

In the preparation of enteric coated tablets, the tablets described in Example 16(a) are given a thin coat of shellac varnish, followed by 20 coats of cellulose acetate phthalate in a manner well known in the art. In a similar manner the capsules of Example 16(b) may be provided with an enteric coating.

EXAMPLE 16(d)

Vials containing a solution of water-soluble compounds of the present invention suitable for injection are prepared from the following ingredients:

| | |
|---|---|
| Active Ingredient | 1100 g |
| Mannitol | 1100 g |
| Water, freshly distilled | to 11 liters |

The active ingredient and mannitol are dissolved in some of the water and the volume of the solution is adjusted to 11 litres. The resulting solution is sterilised by filtration and filled into sterile vials each containing 1.65 ml of solution.

We claim:

1. A compound of the formula (I):

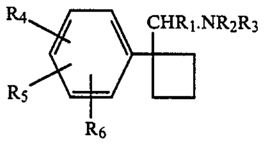

I or a pharmaceutically acceptable salt thereof wherein $R_1$ is furyl, thienyl, pyrrolyl, pyridyl, tetrahydrofuryl, tetrahydrothienyl, thiazolyl, imidazolyl, pyrazolyl, pyrazinyl, pyrimidinyl, pyridazinyl, triazolyl, tetrazolyl or dithianyl, unsubstituted or substituted by one or more substituents selected from the group consisting of alkyl containing 1 to 3 carbon atoms, halo, hydroxy, alkoxy containing 1 to 3 carbon atoms, and trifluoromethyl;

$R_2$ is H, straight or branched chain alkyl containing 1 to 4 carbon atoms, alkenyl containing 3 to 6 carbon atoms or cycloalkyl containing 3 to 7 carbon atoms;

$R_3$ is H, straight chain alkyl containing 1 to 3 carbon atoms or formyl;

$R_4$, $R_5$ and $R_6$ are the same or different and each is H, halo, trifluoromethyl, hydroxy, alkyl containing 1 to 3 carbon atoms, alkylthio containing 1 to 3 carbon atoms or phenyl or $R_4$ and $R_5$, together with the carbon atoms to which they are attached, form a second benzene ring which is unsubstituted or substituted by one or more substituents selected from the group consisting of halo, alkyl containing 1 to 3 carbon atoms and alkoxy containing 1 to 3 carbon atoms or the substituent on the second benzene ring together with the carbon atoms to which they are attached form a further benzene ring.

2. A compound according to claim 1 wherein $R_1$ is substituted by one or more substituents selected from the group consisting of alkyl containing 1 to 3 carbon atoms, halo, alkoxy containing 1 to 3 carbon atoms and trifluoromethyl.

3. A compound according to claim 2, wherein $R_1$ is methylfuryl, methylpyrrolyl, methylimidazolyl, methylpyrazolyl, methyltetrazolyl or methylthiazolyl.

4. A compound according to claim 1 wherein $R_2$ is H, methyl, ethyl, isopropyl, allyl, cyclopropyl, cyclobutyl, cyclopentyl or cyclohexyl.

5. A compound according to claim 1 wherein $R_3$ is H, methyl, ethyl, propyl or isopropyl.

6. A compound according to claim 1 wherein $R_4$, $R_5$ and $R_6$ are the same or different and each is selected from the group consisting of H, fluoro, chloro, bromo, iodo, methyl, methoxy, methylthio and phenyl or $R_4$ and $R_5$ together with the carbon atoms to which they are attached form a second benzene ring unsubstituted or substituted by one or more substituents selected from the group cónsisting of halo, alkyl containing 1 to 3 carbon atoms and alkoxy containing 1 to 3 carbon atoms or the substituents on the second benzene ring together with the carbon atoms to which they are attached form a further benzene ring.

7. A compound according to claim 6 wherein $R_4$ is halo, methyl, methylthio or phenyl and $R_5$ is H or halo or $R_4$ and $R_5$ together with the carbon atoms to which they are attached form a second benzene ring.

8. A compound according to claim 1 in the form of the hydrochloride, maleate, acetate, citrate, fumarate, tartrate, succinate, aspartate or glutamate salt.

9. A compound according to claim 1 which is:

[1-(4-chlorophenyl)cyclobutyl](thien-2-yl)methylamine,

[1-(4-chlorophenyl)cyclobutyl](pyrid-2-yl)methylamine,

[1-(4-chlorophenyl)cyclobutyl](pyrid-3-yl)methylamine,

[1-(4-chlorophenyl)cyclobutyl](pyrid-4-yl)methylamine,

[1-(4-biphenylyl)cyclobutyl](pyrid-2-yl)methylamine,

[1-(3-trifluoromethylphenyl)cyclobutyl](pyrid-3-yl)methylamine,

[1-(4-chlorophenyl)cyclobutyl](thien-3-yl)methylamine,

[1-(4-chloro-3,5-dimethylphenyl)cyclobutyl](pyrid-2-yl)methylamine,

[1-(3,4-dichlorophenyl)cyclobutyl](pyrid-2-yl)methylamine,

[1-(4-methylthiophenyl)cyclobutyl](pyrid-3-yl)methylamine,

[1-(4-fluorophenyl)cyclobutyl](thien-2-yl)methylamine,

[1-(6-chloronaphth-2-yl)cyclobutyl](pyrid-2-yl)methylamine,
[1-(4-chloro-2-fluorophenyl)cyclobutyl](pyrid-3-yl)methylamine,
[1-(4-chlorophenyl)cyclobutyl](1-methylpyrazol-5-yl)methylamine,
[1-(4-chlorophenyl)cyclobutyl](5-methylfur-2-yl)methylamine,
[1-(4-chlorophenyl)cyclobutyl](fur-2-yl)methylamine,
(1-phenylcyclobutyl) (thien-2-yl)methylamine,
[1-(4-biphenynyl)cyclobutyl](thien-2-yl)methylamine,
[1-(4-chlorophenyl)cyclobutyl](1-methylpyrrol-2-yl)methylamine,
[1-(3,4-dichlorophenyl)cyclobutyl](1-methylimidazol2-yl)methylamine,
[1-(3,4-dichlorophenyl)cyclobutyl](thien-2-yl)methylamine,
[1-(4-chlorophenyl)cyclobutyl](1-methylimidazol-2-yl)methylamine,
[1-(naphth-2-yl)cyclobutyl](1-methylimidazol-2-yl)methylamine,
[1-(4-methylphenyl)cyclobutyl](thien-2-yl)methylamine,
[1-(4-methoxyphenyl)cyclobutyl](thien-2-yl)methylamine,
[1-(4-bromophenyl)cyclobutyl](thien-2-yl)methylamine,
[1-(4-iodophenyl)cyclobutyl](thien-2-yl)methylamine,
[1-(4-chlorophenyl)cyclobutyl](4-methylthiazol-2-yl)methylamine,
N,N-dimethyl-[1-(4-chlorophenyl)cyclobutyl](thien-2-yl)methylamine,
N-ethyl-[1-(4-chlorophenyl)cyclobutyl](thien-2-yl)methylamine,
[1-(4-chlorophenyl)cyclobutyl](1,3-dithian-2-yl)methylamine,
[1-(4-chlorophenyl)cyclobutyl](tetrahydrofur-2-yl)methylamine,
N-formyl-[1-(4-biphenylyl)cyclobutyl](pyrid-2-yl)methylamine,
N-methyl-[1-(4-chlorophenyl)cyclobutyl](1-methyl-5-tetrazolyl)methylamine,
N-methyl-[1-(4-chlorophenyl)cyclobutyl](2-methyl-5-tetrazolyl)methylamine,
N-{[1-(3,4-dichlorophenyl)cyclobutyl](2-pyridyl)methyl}cyclopentylamine,
or a pharmaceutically acceptable salt thereof.

10. A pharmaceutical composition useful for treating depression in humans which comprises an anti-depressantly effective amount of a compound of the formula (I):

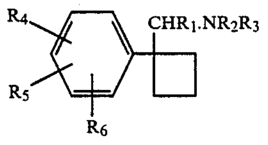

I or a pharmaceutically acceptable salt thereof wherein $R_1$ is a 5- or 6-membered heterocyclic ring containing one or more heteroatoms selected from N, O and S unsubstituted or substituted by one or more substituents selected from the group consisting of alkyl containing 1 to 3 carbon atoms, halo, hydroxy, alkoxy containing 1 to 3 carbon atoms, and trifluoromethyl;

$R_2$ is H, straight or branched chain alkyl containing 1 to 4 carbon atoms, or cycloalkyl containing 3 to 7 carbon atoms;

$R_3$ is H, straight chain alkyl containing 1 to 3 carbon atoms or formyl;

$R_4$, $R_5$ and $R_6$ are the same or different and each is H, halo, trifluoromethyl, hydroxy, alkyl containing 1 to 3 carbon atoms, alkoxy containing 1 to 3 carbon atoms, alkylthio containing 1 to 3 carbon atoms or phenyl or $R_4$ and $R_5$, together with the carbon atoms to which they are attached form a second benzene ring which is unsubstituted or substituted by one or more substituents selected from the group consisting of halo, alkyl containing 1 to 3 carbon atoms and alkoxy containing 1 to 3 carbon atoms or the substituent on the second benzene ring together with the carbon atoms to which they are attached form a further benzene ring, in combination with a pharmaceutically acceptable carrier.

11. A composition according to claim 10 wherein $R_1$ is a 5- or 6-membered heterocyclic ring containing one heteroatom selected from N, O and S.

12. A composition according to claim 10 wherein $R_1$ is a 5- or 6-membered heterocyclic ring containing two or more heteroatoms which are the same or different selected from N, O and S.

13. A composition according to claim 10 wherein $R_1$ is furyl, thienyl, pyrrolyl, pyridyl, tetrahydrofuryl, tetrahydrothienyl, thiazolyl, imidazolyl, pyrazolyl, pyrazinyl, pyrimidinyl, pyridazinyl, triazolyl, tetrazolyl or dithianyl.

14. A composition according to claim 10 wherein the compound is
[1-(4-chlorophenyl)cyclobutyl](thien-2-yl)methylamine,
[1-(4-chlorophenyl)cyclobutyl](pyrid-2-yl)methylamine,
[1-(4-chlorophenyl)cyclobutyl](pyrid-3-yl)methylamine,
[1-(4-chlorophenyl)cyclobutyl](pyrid-4-yl)methylamine,
[1-(4-biphenylyl)cyclobutyl](pyrid-2-yl)methylamine,
[1-(3-trifluoromethylphenyl)cyclobutyl](pyrid-3-yl)methylamine,
[1-(4-chlorophenyl)cyclobutyl](thien-3-yl)methylamine,
[1-(4-chloro-3,5-dimethylphenyl)cyclobutyl](pyrid-2-yl)methylamine,
[1-(3,4-dichlorophenyl)cyclobutyl](pyrid-2-yl)methylamine,
[1-(4-methylthiophenyl)cyclobutyl](pyrid-3-yl)methylamine,
[1-(4-fluorophenyl)cyclobutyl](thien-2-yl)methylamine,
[1-(6-chloronaphth-2-yl)cyclobutyl](pyrid-2-yl)methylamine,
[1-(4-chloro-2-fluorophenyl)cyclobutyl](pyrid-3-yl)methylamine,
[1-(4-chlorophenyl)cyclobutyl](1-methylpyrazol-5-yl)methylamine,
[1-(4-chlorophenyl)cyclobutyl](5-methylfur-2-yl)methylamine,
[1-(4-chlorophenyl)cyclobutyl](fur-2-yl)methylamine,
(1-phenylcyclobutyl) (thien-2-yl)methylamine,
[1-(4-biphenynyl)cyclobutyl](thien-2-yl)methylamine,
[1-(4-chlorophenyl)cyclobutyl](1-methylpyrrol-2-yl)methylamine,
[1-(3,4-dichlorophenyl)cyclobutyl](1-methylimidazol2-yl)methylamine,

[1-(3,4-dichlorophenyl)cyclobutyl](thien-2-yl)methylamine,
[1-(4-chlorophenyl)cyclobutyl](1-methylimidazol-2-yl)methylamine,
[1-(naphth-2-yl)cyclobutyl](1-methylimidazol-2-yl)methylamine,
[1-(4-methylphenyl)cyclobutyl](thien-2-yl)methylamine,
[1-(4-methoxyphenyl)cyclobutyl](thien-2-yl)methylamine,
[1-(4-bromophenyl)cyclobutyl](thien-2-yl)methylamine,
[1-(4-iodophenyl)cyclobutyl](thien-2-yl)methylamine,
[1-(4-chlorophenyl)cyclobutyl](4-methylthiazol-2-yl)methylamine,
N,N-dimethyl-[1-(4-chlorophenyl)cyclobutyl](thien-2-yl)methylamine,
N-ethyl-[1-(4-chlorophenyl)cyclobutyl](thien-2-yl)methylamine,
[1-(4-chlorophenyl)cyclobutyl](1,3-dithian-2-yl)methylamine,
[1-(4-chlorophenyl)cyclobutyl](tetrahydrofur-2-yl)methylamine,
N-formyl-[1-(4-biphenylyl)cyclobutyl](pyrid-2-yl)methylamine,
N-methyl-[1-(4-chlorophenyl)cyclobutyl](1-methyl-5-tetrazolyl)methylamine,
N-methyl-[1-(4-chlorophenyl)cyclobutyl](2-methyl-5-tetrazolyl)methylamine,
N-{[1-(3,4-dichlorophenyl)cyclobutyl](2-pyridyl)methyl}cyclopentylamine, or a pharmaceutically acceptable salt thereof.

15. A method of treating depression in human which comprises administering to a human in need thereof an anti-depressently effective amount of a compound of the formula (I):

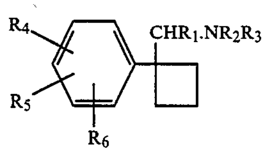

I or a pharmaceutically acceptable salt thereof wherein $R_1$ is a 5- or 6-membered heterocyclic ring containing one or more heteroatoms selected from N, O and S unsubstituted or substituted by one or more substituents selected from the group consisting of alkyl containing 1 to 3 carbon atoms, halo, hydroxy, alkoxy containing 1 to 3 carbon atoms, and trifluoromethyl;

$R_2$ is H, straight or branched chain alkyl containing 1 to 4 carbon atoms, or cycloalkyl containing 3 to 7 carbon atoms;

$R_3$ is H, straight chain alkyl containing 1 to 3 carbon atoms or formyl;

$R_4$, $R_5$ and $R_6$ are the same or different and each is H, halo, trifluoromethyl, hydroxy, alkyl containing 1 to 3 carbon atoms, alkoxy containing 1 to 3 carbon atoms, alkylthio containing 1 to 3 carbon atoms or phenyl or $R_4$ and $R_5$, together with the carbon atoms to which they are attached form a second benzene ring which is unsubstituted or substituted by one or more substituents selected from the group consisting of halo, alkyl containing 1 to 3 carbon atoms and alkoxy containing 1 to 3 carbon atoms or the substituent on the second benzene ring together with the carbon atoms to which they are attached form a further benzene ring, in combination with a pharmaceutically acceptable carrier.

16. A method according to claim 15 wherein $R_1$ is a 5- or 6-membered heterocyclic ring containing one heteroatom selected from N, O and S.

17. A method according to claim 15 wherein $R_1$ is a 5- or 6-membered heterocyclic ring containing two or more heteroatoms which are the same or different selected from N, O and

18. A method according to claim 15 wherein $R_1$ is furyl, thienyl, pyrrolyl, pyridyl, tetrahydrofuryl, tetrahydrothienyl, thiazolyl, imidazolyl, pyrazolyl, pyrazinyl, pyrimidinyl, pyridazinyl, triazolyl, tetrazolyl or dithianyl.

19. A method according to claim 15 wherein the compound is

[1-(4-chlorophenyl)cyclobutyl](thien-2-yl)methylamine,
[1-(4-chlorophenyl)cyclobutyl](pyrid-2-yl)methylamine,
[1-(4-chlorophenyl)cyclobutyl](pyrid-3-yl)methylamine,
[1-(4-chlorophenyl)cyclobutyl](pyrid-4-yl)methylamine,
[1-(4-biphenylyl)cyclobutyl](pyrid-2-yl)methylamine,
[1-(3-trifluoromethylphenyl)cyclobutyl](pyrid-3-yl)methylamine,
[1-(4-chlorophenyl)cyclobutyl](thien-3-yl)methylamine,
[1-(4-chloro-3,5-dimethylphenyl)cyclobutyl](pyrid-2-yl)methylamine,
[1-(3,4-dichlorophenyl)cyclobutyl](pyrid-2-yl)methylamine,
[1-(4-methylthiophenyl)cyclobutyl](pyrid-3-yl)methylamine,
[1-(4-fluorophenyl)cyclobutyl](thien-2-yl)methylamine,
[1-(6-chloronaphth-2-yl)cyclobutyl](pyrid-2-yl)methylamine,
[1-(4-chloro-2-fluorophenyl)cyclobutyl](pyrid-3-yl)methylamine,
[1-(4-chlorophenyl)cyclobutyl](1-methylpyrazol-5-yl)methylamine,
[1-(4-chlorophenyl)cyclobutyl](5-methylfur-2-yl)methylamine,
[1-(4-chlorophenyl)cyclobutyl](fur-2-yl)methylamine,
(1-phenylcyclobutyl) (thien-2-yl)methylamine,
[1-(4-biphenynyl)cyclobutyl](thien-2-yl)methylamine,
[1-(4-chlorophenyl)cyclobutyl](1-methylpyrrol-2-yl)methylamine,
[1-(3,4-dichlorophenyl)cyclobutyl](1-methylimidazol2-yl)methylamine,
[1-(3,4-dichlorophenyl)cyclobutyl](thien-2-yl)methylamine,
[1-(4-chlorophenyl)cyclobutyl](1-methylimidazol-2-yl)methylamine,
[1-(naphth-2-yl)cyclobutyl](1-methylimidazol-2-yl)methylamine,
[1-(4-methylphenyl)cyclobutyl](thien-2-yl)methylamine,
[1-(4-methoxyphenyl)cyclobutyl](thien-2-yl)methylamine,
[1-(4-bromophenyl)cyclobutyl](thien-2-yl)methylamine,

[1-(4-iodophenyl)cyclobutyl](thien-2-yl)methylamine,

[1-(4-chlorophenyl)cyclobutyl](4-methylthiazol-2-yl)methylamine,

N,N-dimethyl-[1-(4-chlorophenyl)cyclobutyl](thien-2-yl)methylamine,

N-ethyl-[1-(4-chlorophenyl)cyclobutyl](thien-2-yl)methylamine,

[1-(4-chlorophenyl)cyclobutyl](1,3-dithian-2-yl)methylamine,

[1-(4-chlorophenyl)cyclobutyl](tetrahydrofur-2-yl)methylamine,

N-formyl-[1-(4-biphenylyl)cyclobutyl](pyrid-2-yl)methylamine,

N-methyl-[1-(4-chlorophenyl)cyclobutyl](1-methyl-5-tetrazolyl)methylamine,

N-methyl-[1-(4-chlorophenyl)cyclobutyl](2-methyl-5-tetrazolyl)methylamine,

N-{[1-(3,4-dichlorophenyl)cyclobutyl](2-pyridyl)methyl}cyclopentylamine, or a pharmaceutically acceptable salt thereof.

20. A composition according to claim 10 wherein $R_1$ is thiazolyl.

21. A composition according to claim 10 wherein $R_1$ is substituted by one or more substituents selected from the group consisting of alkyl containing 1 to 3 carbon atoms, halo, alkoxy containing 1 to 3 carbon atoms and trifluoromethyl.

22. A composition according to claim 10 wherein $R_1$ is methylfuryl, methylpyrrolyl, methylimidazolyl, methylpyrazolyl, methyltetrazolyl or methylthiazolyl.

23. A composition according to claim 10 wherein $R_2$ is H, methyl, ethyl, isopropyl, allyl, cyclopropyl, cyclobutyl, cyclopentyl or cyclohexyl.

24. A composition according to claim 10 wherein $R_3$ is H, methyl, ethyl, propyl or isopropyl.

25. A composition according to claim 10 wherein $R_4$, $R_5$ and $R_6$ are the same or different and each is selected from the group consisting of H, fluoro, chloro, bromo, iodo, methyl, methoxy, methylthio and phenyl, or $R_4$ and $R_5$ together with the carbon atoms to which they are attached form a second benzene ring unsubstituted or substituted by one or more substituents selected from the group consisting of halo, alkyl containing 1 to 3 carbon atoms and alkoxy containing 1 to 3 carbon atoms or the substituents on the second benzene ring together with the carbon atoms to which they are attached form a further benzene ring.

26. A composition according to claim 10 wherein $R_4$ is halo, methyl, methylthio or phenyl and $R_5$ is H or halo or $R_4$ and $R_5$ together with the carbon atoms to which they are attached form a second benzene ring.

27. A composition according to claim 10 wherein the compound is in the form of the hydrochloride, maleate, acetate, citrate, fumarate, tartrate, succinate, aspartate or glutamate salt.

28. A method according to claim 15 wherein $R_1$ is thiazolyl.

29. A method according to claim 15 wherein $R_1$ is substituted by one or more substituents selected from the group consisting of alkyl containing 1 to 3 carbon atoms, halo, alkoxy containing 1 to 3 carbon atoms and trifluoromethyl.

30. A method according to claim 15 wherein $R_1$ is methylfuryl, methylpyrrolyl, methylimidazolyl, methylpyrazolyl, methyltetrazolyl or methylthiazolyl.

31. A method according to claim 15 wherein $R_2$ is H, methyl, ethyl, isopropyl, allyl, cyclopropyl, cyclobutyl, cyclopentyl or cyclohexyl.

32. A method according to claim 15 wherein $R_3$ is H, methyl, ethyl, propyl or isopropyl.

33. A method according to claim 15 wherein $R_4$, $R_5$ and $R_6$ are the same or different and each is selected from the group consisting of H, fluoro, chloro, bromo, iodo, methyl, methoxy, methylthio and phenyl, or $R_4$ and $R_5$ together with the carbon atoms to which they are attached form a second benzene ring unsubstituted or substituted by one or more substituents selected from the group consisting of halo, alkyl containing 1 to 3 carbon atoms and alkoxy containing 1 to 3 carbon atoms or the substituents on the second benzene ring together with the carbon atoms to which they are attached form a further benzene ring.

34. A method according to claim 15 wherein $R_4$ is halo, methyl, methylthio or phenyl and $R_5$ is H or halo or $R_4$ and $R_5$ together with the carbon atoms to which they are attached form a second benzene ring.

35. A method according to claim 15 wherein the compound is in the form of the hydrochloride, maleate, acetate, citrate, fumarate, tartrate, succinate, aspartate or glutamate salt.

36. A compound according to claim 1, wherein $R_1$ is thiazolyl.

* * * * *